United States Patent

Mamedov et al.

(10) Patent No.: US 6,710,011 B2
(45) Date of Patent: Mar. 23, 2004

(54) CATALYST COMPOSITIONS FOR THE AMMOXIDATION OF ALKANES AND OLEFINS, METHODS OF MAKING AND OF USING SAME

(75) Inventors: Edouard A. Mamedov, Houston, TX (US); Kathleen A. Bethke, Sugar Land, TX (US); Shahid N. Shaikh, Houston, TX (US); Armando Araujo, Houston, TX (US); Neeta K. Kulkarni, Houston, TX (US); Andrei Khodakov, d'Ascq Cedex (FR)

(73) Assignee: Saudi Basic Industries Corporatioin, Riyadh (SA)

( * ) Notice: Subject to any disclaimer, the term of this patent is extended or adjusted under 35 U.S.C. 154(b) by 11 days.

(21) Appl. No.: 10/036,866

(22) Filed: Dec. 21, 2001

(65) Prior Publication Data

US 2003/0144539 A1 Jul. 31, 2003

(51) Int. Cl.⁷ ................................. B01J 23/20
(52) U.S. Cl. ....................................... 502/353
(58) Field of Search ......................... 502/353

(56) References Cited

U.S. PATENT DOCUMENTS

| | | |
|---|---|---|
| 3,860,534 A | 1/1975 | Harris et al. |
| 4,746,641 A | 5/1988 | Guttmann et al. |
| 4,784,979 A | 11/1988 | Toft et al. |
| 4,797,381 A | 1/1989 | Bartek et al. |
| 4,871,706 A | 10/1989 | Brazdil, Jr. et al. |
| 4,873,215 A | 10/1989 | Brazdil et al. |
| 4,879,264 A | 11/1989 | Toft et al. |
| 4,888,438 A | 12/1989 | Glaeser et al. |
| 5,008,427 A | 4/1991 | Brazdil, Jr. et al. |
| 5,079,207 A | 1/1992 | Brazdil et al. |
| 5,094,989 A | 3/1992 | Lynch et al. |
| 5,214,016 A | 5/1993 | Brazdil et al. |
| 5,332,855 A | 7/1994 | Blanchard et al. |
| 5,336,804 A | 8/1994 | Blanchard et al. |
| 5,498,588 A | 3/1996 | Brazdil et al. |
| 5,576,469 A | 11/1996 | Brazdil, Jr. et al. |
| 5,693,587 A | 12/1997 | Brazdil, Jr. et al. |
| 5,854,172 A | 12/1998 | Brazdil, Jr. et al. |
| 5,994,259 A | 11/1999 | Brazdil, Jr. et al. |
| 6,072,070 A | 6/2000 | Albonetti et al. |
| 6,083,869 A | 7/2000 | Albonetti et al. |
| 6,156,920 A | 12/2000 | Brazdil, Jr. et al. |
| 6,162,760 A | 12/2000 | Brazdil, Jr. |

FOREIGN PATENT DOCUMENTS

| | | |
|---|---|---|
| GB | 1336136 | 11/1973 |
| WO | WO 00/12208 | 3/2000 |

OTHER PUBLICATIONS

"An Investigation of the Al–Sb–V–W–Oxide System for Propane Ammoxidation," J. Nilsson et al, Journal of Catalysis, 186, p. 442–457 (1999).

Primary Examiner—Joseph K. McKane
Assistant Examiner—Kamal Saeed
(74) Attorney, Agent, or Firm—Jim Wheelington

(57) ABSTRACT

A catalyst composition for the vapor phase ammoxidation of alkanes and olefins of the general empirical formulae:

$$VSb_aM_bO_x$$

$$VSb_aM_bM'_{b'}O_x$$

$$VSb_aM_bQ_cO_x$$

$$VSb_aM_bQ_cQ'_{c'}O_x$$

wherein M and M' are at least one element selected from magnesium, aluminum, zirconium, silicon, hafnium, titanium and niobium, M and M' being different, Q and Q' are at least one element selected from rhenium, tungsten, molybdenum, tantalum, manganese, phosphorus, cerium, tin, boron, scandium, bismuth, gallium, indium, iron, chromium, lanthanum, yttrium, zinc, cobalt, nickel, cadmium, copper, strontium, barium, calcium, silver, potassium, sodium and cesium, Q and Q' being different, a is 0.5 to 20, b is 2 to 50, b' is 0 to 50, c is 0 to 10, c' is 0 to 10 and x is determined by the valence requirements of the elements present. The catalyst composition containing isolated vanadium and antimony species in an inert matrix is prepared by incorporating respective compounds of vanadium and antimony into the oxide of at least one or more M and adding by co-precipitation or impregnation one or more optional Q in the relative atomic proportions indicated by the subscripts.

128 Claims, 1 Drawing Sheet

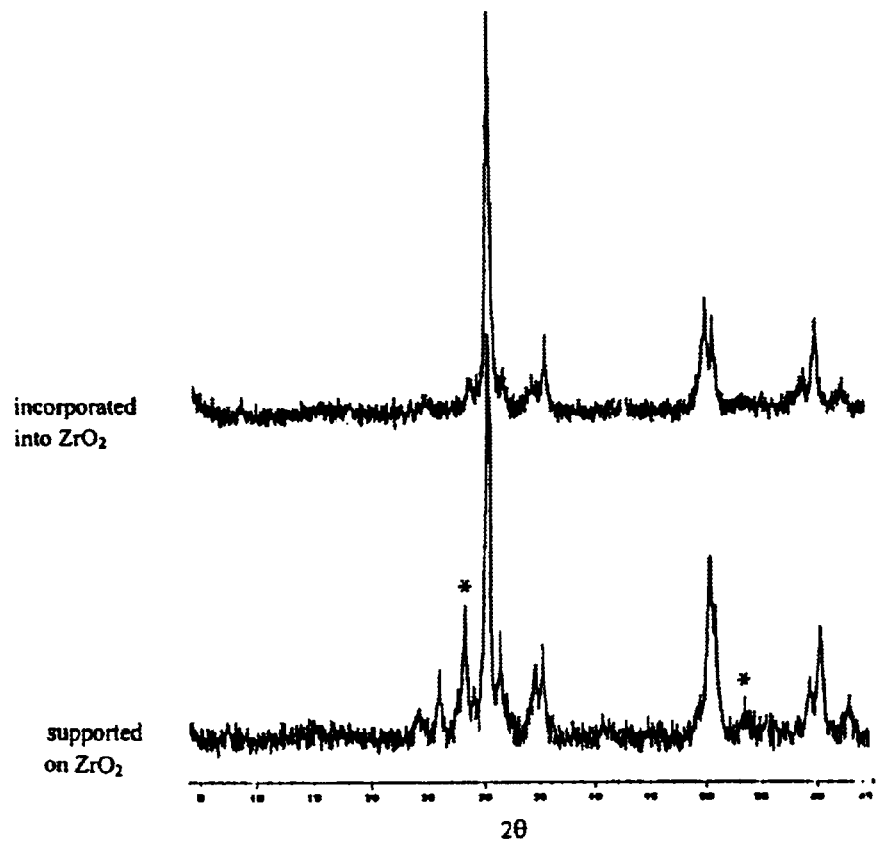
Figure 1. XRD patterns of the VSb$_5$ oxides incorporated in and supported on ZrO$_2$ where * denotes VSbO$_4$ phase

CATALYST COMPOSITIONS FOR THE AMMOXIDATION OF ALKANES AND OLEFINS, METHODS OF MAKING AND OF USING SAME

BACKGROUND OF THE INVENTION

1. Field of the Invention

The invention relates to a catalyst for the catalytic ammoxidation of alkanes and olefins, more specifically $C_3$ to $C_5$ paraffins or olefins, such as propane or isobutane and propylene or isobutylene, to the corresponding $\alpha,\beta$-unsaturated mononitriles, e.g., acrylonitrile and methacrylonitrile, utilizing the disclosed catalyst. In addition, the catalyst may be used in the ammoxidation of xylenes and methylpyridines to the corresponding mono- and di-nitriles.

The invention is directed also to making the catalyst containing isolated vanadium and antimony species in a matrix formed by the oxides of elements usually used as supports or diluents. The invention is directed also to using the catalyst in a process for catalytic ammoxidation of alkanes and olefins.

2. Description of the Prior Art

Acrylonitrile is industrially prepared from the ammoxidation of propylene over a metal oxide catalyst. Due to the lower cost of propane compared with propylene, much research attention has been directed towards finding a catalyst selective for the formation of acrylonitrile from propane. The majority of such catalysts are based on V-Sb oxides.

U.S. Pat. No. 3,860,534 discloses the use for ammoxidation of propane of catalysts containing only vanadium and antimony in oxidic form. British Patent No. 1,336,136 teaches that catalysts can contain, beside vanadium and antimony, only one other metal, which is disclosed to be tin. U.S. Pat. No. 4,746,641 discloses paraffin ammoxidation catalysts that contain tungsten in addition to vanadium and antimony and, optionally, tin, boron, molybdenum, gallium, iron, cobalt, nickel, chromium, manganese, zinc, selenium, tellurium, arsenic, calcium, strontium, bariun or thallium. U.S. Pat. Nos. 4,784,979 and 4,879,264 disclose processes for making a vanadium-antimony catalyst. U.S. Pat. No. 4,797,381 discloses a V-Sb based catalyst with at least one of tungsten, tin, molybdenum, boron, phosphorus, germanium, copper, silver, niobium, tantallum, titanium, iron, cobalt, nickel, chromium, lead, manganese, zinc, selenium, tellurium, gallium, indium, arsenic, an alkali metal, an alkaline earth metal or a rare earth. U.S. Pat. No. 4,871,706 discloses a vanadium-antimony catalyst with tungsten and phosphorus. U.S. Pat. No. 4,873,215 discloses tungsten and phosphorus in addition to vanadium and antimony without molybdenum in a catalyst supported on silica-alumina or alumina. U.S. Pat. No. 4,888,438 discloses a vanadium-antimony catalyst having tungsten, tin, molybdenum, boron, phosphorus or germanium and, optionally, iron, cobalt, nickel, chromium, lead, manganese, zinc, selenium, tellurium, gallium, indium, arsenic, an alkali metal, thallium, magnesium, calcium, strontium, or barium. U.S. Pat. No. 5,008,427 discloses a process of using a catalyst with titanium, tin, iron, chromium or gallium in addition to vanadium and antimony. U.S. Pat. No. 5,079,207 discloses a catalyst with tellurium or bismuth in addition to vanadium-antimony. U.S. Pat. No. 5,094,989 discloses a catalyst having an atomic ratio of antimony:vanadium is a specific range. U.S. Pat. Nos. 5,214,016 and 5,854,172 disclose a vanadium-antimony-tin catalyst. U.S. Pat. No. 5,332,855 discloses a vanadium-antimony catalyst optionally containing iron, gallium, indium or mixtures thereof. U.S. Pat. No. 5,336,804 discloses a vanadium-antimony-bismuth catalyst optionally containing iron, gallium, indium or mixtures thereof. U.S. Pat. No. 5,498,588 discloses a catalyst with vanadium and antimony with titanium, tin, iron, chromium, gallium, lithium, magnesium, calcium, strontium, barium, cobalt, nickel, zinc, germanium, niobium, zirconium, molybdenum, tungsten, copper, tellurium, tantalum, selenium, bismuth, cerium, indium, arsenic, boron or manganese impregnated with lithium, silver, iron, cobalt, copper, chromium, manganese, $(VO)^{2+}$ $(PW_{12}O_{40})^{3-}$ or $(PMo_{12}O_{40})^{3-}$. U.S. Pat. Nos. 5,576,469 and 5,693,587 disclose a vanadium-antimony catalyst optionally having tin, titanium, lithium, magnesium, sodium, calcium, strontium, barium, cobalt, iron, chromium, gallium, nickel, zinc, germanium, niobium, zirconium, molybdenum, tungsten, copper, tellurium, tantalum, selenium, bismuth, cerium, indium, arsenic, boron, aluminum, phosphorus or manganese. U.S. Pat. No. 5,994,259 discloses a vanadium-antimony based catalyst in which tin, titanium or iron are optionally present. U.S. Pat. No. 6,072,070 discloses a vanadium-antimony-titanium catalyst containing $TiO_2$ species. U.S. Pat. No. 6,083,869 discloses a co-precipitated vanadium-antimony-iron catalyst. U.S. Pat. No. 6,156,920 discloses a vanadium-antimony based catalyst which titanium, tin, iron, chromium or gallium must be present and lithium, magnesium, calcium, strontium, barium, cobalt, nickel, zinc, germanium, niobium, zirconium, tungsten, copper, tellurium, tantalum, selenium, bismuth, cerium, indium, arsenic, boron, manganese or molybdenum are optionally present. U.S. Pat. No. 6,162,760 discloses a vanadium-antimony based catalyst in which molybdenum, tungsten, niobium, arsenic, tellurium or selenium must be present and lithium, magnesium, calcium, strontium, barium, cobalt, nickel, zinc, germanium, zirconium, copper, tantalum, bismuth, cerium, indium, boron or manganese are optionally present.

Vanadium-antimony-based oxide catalysts claimed for the use in the process of ammoxidation of alkanes can comprise a single or a number of mixed vanadium, antimony and other oxides, constituting the active phase of the catalyst, or can additionally comprise another inorganic oxide, such as alumina, silica, zirconia, magnesia, titania or niobia, on which the active phase is deposited, e.g., U.S. Pat. No. 4,797,381, or with which the to active phase is mixed, e.g., U.S. Pat. No. 4,871,706, by using various techniques known in the art, such as impregnation or slurry deposition. Oxides used as supports or diluents in the catalyst art are mostly employed to improve catalyst abrasion resistance and/or to reduce its cost and do not substantially affect catalytic behavior of the active phase. The general formula of catalysts in patents do not usually include support material.

None of the above patent documents describe the use of support material as a matrix for isolation of V and Sb species in the catalyst. PCT International Application published under the number WO 00/12208 discloses vanadium antimony oxides (5 mole % of each) dispersed in and distributed by sol-gel method throughout a matrix comprising oxides of silicon, titanium, tantalum and niobium, for using as catalysts for the oxidation of butadiene to furan. There is no mention of the usefulness of these catalysts for ammoxidation reactions. Also, the patent does not disclose or suggest the vanadium antimony oxides implanted into alumina, magnesia, zirconia and hafnia to be useful catalysts. Some indication that alumina can be used as a matrix material comes from the data on propane ammoxidation over vanadium-antimony, vanadium-antimony-aluminum and vanadium-antimony-tungsten-aluminum oxide catalysts recently published by J. Nilsson et. al in *J. Catalysis,* 1999, 186, 442. The present invention discloses that the incorporation of oxides vanadium and antimony into an inert oxide matrix, such as alumina, zirconia, magnesia and others, improves catalytic behavior in propane ammoxidation in terms of both stability and selectivity of catalyst activity.

SUMMARY OF THE INVENTION

The present invention provides mixed metal oxide catalysts containing vanadium and antimony for the ammoxidation of paraffins to unsaturated mononitriles, in particular the amoxidation of propane and isobutane to acrylonitrile and methacrylonitrile, respectively.

The present invention provides a method for preparing mixed metal oxide catalysts containing isolated vanadium and antimony species in an inert matrix.

The present invention provides an ammoxidation process for making unsaturated mononitriles from lower paraffins, in particular for the producing acrylonitrile and methacrylonitrile from propane and isobutane, using mixed metal oxide catalysts containing vanadium and antimony in an inert matrix.

Embodiments, aspects, features and advantages of the present invention will become apparent from the study of the accompanying disclosure and appended claims.

According to one aspect of the invention, there is provided a catalyst composition comprising the elements in proportions indicated by the following empirical formula:

$$VSb_aM_bO_x$$

where M is at least one element selected from magnesium, aluminum, zirconium, silicon, hafnium, titanium and niobium;

$0.5 \leq a \leq 20$ $2 \leq b \leq 50$ and x is determined by the valence requirements of the elements present.

In related aspects of the present invention, there are provided catalyst compositions comprising elements in proportions indicated by the following empirical formulae:

$$VSb_aM_bM'_{b'}O_x$$

$$VSb_aM_bQ_cO_x$$

$$VSb_aM_bQ_cQ'_{c'}O_x$$

where M' is selected from magnesium, aluminum, zirconium, silicon, hafnium, titanium and niobium, M and M' are different and $0 \leq b' \leq 50$; Q and Q' are each one or more elements selected from rhenium, tungsten, molybdenum, tantalum, manganese, phosphorus, cerium, tin, boron, scandium, bismuth, gallium, indium, iron, chromium, lanthanum, yttrium, zinc, cobalt, nickel, cadmium, copper, strontium, barium, calcium, silver, potassium, sodium and cesium, Q and Q' are different, $0 \leq c \leq 10$ and $0 \leq c' \leq 10$; M, a, b and x are as defined above.

In another aspect of the present invention, there are methods of preparing catalysts having the following empirical formulae:

$$VSb_aM_bO_x$$

$$VSb_aM_bM'_{b'}O_x$$

$$VSb_aM_bQ_cO_x$$

$$VSb_aM_bQ_cQ'_{c'}O_x$$

where M, M', Q, Q', a, b, b', c, c' and x are as defined above. The methods comprise precipitating mixed hydroxides from a solution or suspension of vanadium, antimony, M, M', Q and Q' compounds as desired to obtain a particular catalyst composition, removing solvent from the precipitate to form a dried catalyst precursor, and calcining the resultant dried precursor at a final temperature in the range of 600 to 950° C. to form the catalyst containing isolated V and Sb species in the $M_tO_x$ or $M_tM'_{t'}O_x$ matrix. In an alternative to the Q and Q' elements being added and precipitated with the other elements, one or both may be impregnated on the $VSb_aM_c$ solid before or after calcination.

The present invention also provides a process for making α,β-unsaturated mononitriles by gas phase reaction of propane or isobutane, oxygen and ammonia in the presence of a catalyst having the elements and proportions indicated by the empirical formulae:

$$VSb_aM_bO_x$$

$$VSb_aM_bM'_{b'}O_x$$

$$VSb_aM_bQ_cO_x$$

$$VSb_aM_bQ_cQ'_{c'}O_x$$

where M, M', Q, Q', a, b, b', c, c' and x are as defined above.

The catalyst may also be used in the ammoxidation of propylene and isobutylene to acrylonitrile and methacrylonitrile, and in the ammoxidation of xylenes and methylpyridines to the corresponding mono- and/or di-nitriles.

BRIEF DESCRIPTION OF THE DRAWINGS

A more complete appreciation of the invention and many of the attendant advantages thereof will be readily understood by reference to the following detailed description when considered in connection with the accompanying drawing wherein:

FIGURE shows X-ray diffraction (XRD) patterns of a catalyst having $VSb_5$ oxides incorporated with $ZrO_5$ the catalyst and a catalyst having $VSb_5$ supported on $ZrO_2$

DESCRIPTION OF EMBODIMENTS OF THE INVENTION

In the present invention, a catalyst precursor is prepared by precipitation of hydroxides from a solution of compounds of vanadium, antimony, M (which is understood to include M' as appropriate in this description) and, optionally, Q (which is understood to include Q' as appropriate in this description). In this description, "solution" includes not only a solution wherein a solute is completely dissolved but also a solution in a slurry state wherein a part of the solute is present undissolved.

The vanadium, antimony, M and Q compounds are preferably soluble in water, saturated alcohol or a mixture of water and alcohol. When a compound is insoluble in water, an acid or alkali may be used for dissolving it, or the solution may be heated to a temperature of from 50 to 90° C. to facilitate the dissolution. Generally, a solution can be prepared by dissolving two and more compounds, for instance by adding the antimony compound to the solution of the compound containing M. In the alternative, solutions of each of the vanadium, antimony or M compounds were prepared separately.

Exemplary soluble vanadium compounds include ammonium metavanadate, vanadyl acetylacetonate, vanadyl chloride, vanadium pentafluoride and other vanadium halides. Exemplary soluble antimony compounds include antimony oxide, antimony oxychloride, antimony trichloride, antimony pentachloride and other antimony halides. The compound containing an element represented by M can be a nitrate, chloride, carbonate, oxalate, hydroxide and other preferably soluble compounds. Similar compounds can serve as a source for an element represented by Q.

The solution thus obtained is then added and mixed with base to precipitate metal hydroxides. This procedure can be carried out by adding an aqueous solution of an ammonium hydroxide, ammonium carboxylate (e.g., ammonium acetate, ammonium tartrate or ammonium citrate), urea or alcohol. A pH of from 5 to 10 is attained and, preferably, maintained. It is more preferred to have a pH of about 8. To maintain the pH level, it may be necessary to progressively neutralize the acidity possibly formed during the precipitation of metal hydroxides (e.g., hydrohalic acid is formed when a halide of antimony is used) using a basic compound. In the process of making the invention, it is preferable to carry out this neutralization by adding aqueous ammonium hydroxide to the precursor solution or vice versa.

After precipitation of the metal hydroxides of the invention, they are separated from the solvent liquid by any conventional technique, in particular for the present invention by filtration or evaporation. The isolated metal hydroxides are then dried at atmospheric pressure at a temperature ranging from 30 to 200° C., preferably from 100 to 150° C.

The dried hydroxides are calcined with final temperatures ranging from 600 to 950° C., most preferably from 650 to 850° C., in different atmospheres, preferably in air.

The composite oxides of vanadium, antimony, M and Q thus obtained can comprise individual and mixed oxide phases, predominantly containing antimony and elements represented by M. It is believed that the presence of mixed oxides of M elements with antimony, such as $Mg_2Sb_2O_7$, $AlSbO_4$ and $Nb_3Sb_3O_{13}$, infers that they do not play a mere role of support or diluent but do constitute with vanadium and antimony a part of the catalytically active components. Another feature of these compositions revealed by X-ray diffraction (XRD) is the absence of vanadium-containing phases (denoted by an "*") which indicates isolation of vanadium sites in the catalyst composition. As shown in the FIGURE, a catalyst which is supported on zirconia ($ZrO_5$) has peaks as denoted with "*" while a catalyst which has $ZrO_5$ incorporated into the catalyst as disclosed in the present invention does not exhibit these distinctive peaks. These findings indicate that the catalyst composition of the present invention is different from compact and supported vanadium-antimony oxides of prior art catalysts which usually contain $VSbO_4$ phases in the morphology of the active components effective for the ammoxidation reaction.

Compounds containing Q elements can either be added before precipitation or impregnated on the $VSb_aM_b$ oxide before or after the calcination step. If a compound containing Q element(s) is added to calcined $VSb_aM_b$ oxide, the resulting solid may again be calcined at a temperature up to 950° C. but preferably under 850° C.

The catalyst can be employed in the powder form or be shaped, e.g., beads, spheres, pellets, extrudes or crushed particles, according to various techniques known in the art. In the examples of invention below, freshly prepared catalysts were ground to fine powder, tabletted at 20 Kpsi, crushed, sieved to 18–30 mesh and loaded to the reactor.

In the ammoxidation process of the present invention, the reaction is run in the gas phase by contacting a mixture containing paraffin, ammonia and molecular oxygen, and diluent, if any, in a fixed bed of catalyst, or a fluidized bed, or a moving bed (riser reactor). The mole ratio of paraffin to ammonia is usually in the range from 0.5 to 10, preferably from 1 to 2.5, and the mole ratio of paraffin to oxygen is usually from 0.1 to 10, preferably from 0.5 to 2. The mole ratio of gaseous diluent, e.g., $N_2$, He, Ar, $CO_2$ and $H_2O$, to paraffin usually ranges from 0 to 20, preferably from 0 to 10. Higher molar ratios can be used but are usually uneconomical.

In the present process, the paraffin as the starting material is not particularly limited, and it may be any lower alkane having from 2 to 8 carbon atoms. However, from the viewpoint of industrial application of the obtainable nitrites, it is preferred to employ propane or isobutane. Low-weight olefins, such as propylene and isobutylene, can also be employed for production of acrylonitrile and methacrylonitrile, respectively. The process according to the invention is more particularly suitable for the ammoxidation of propane.

The reaction temperature range can vary from 350 to 550° C., preferably from 425 to 500° C. The latter temperature range is especially useful in the case of propane ammoxidation to acrylonitrile.

The pressure of the reaction can be greater than or equal to atmospheric pressure and can range from 1 to 40 psig. Preferably, pressure is 1 to 20 psig.

The effective contact time is in the range from 0.01 to 10 seconds, but is preferably from 0.05 to 8 seconds, more preferably from 0.1 to 5 seconds.

The most advantageous combination of temperature, pressure and contact time for a given desired result from a given feed can be determined by routine experimentation.

The present invention is described in further detail in the following Examples. However, it should be understood that the present invention is by no means restricted to such specific Examples.

COMPARATIVE EXAMPLE 1

Nominal Composition $VSb_9O_x$ 1.75 g $NH_4VO_3$ was dissolved in 90 mL water at 80° C. Meanwhile, 30.59 g $SbCl_3$ was dissolved in 60 mL diluted nitric acid with a $HNO_3$ to $H_2O$ volume ratio of 1:3. The $SbCl_3$ solution was added to the 80° C. $NH_4VO_3$ solution and heating was stopped. The mixture was stirred for 30 min. 30% $NH_4OH$ solution was added dropwise until a pH of 8 was obtained. The solid was filtered and then washed with 260 mL of water. The solid was calcined in a muffle furnace with flowing air. The temperature was increased at 5° C./min to 120° C. and held at this temperature for 5 h. It was then heated at 20° C./min to 427° C. and held at this temperature for 4 h. The temperature was further increased at 20° C./min to 650° C. and held at this temperature for 4.5 h. The catalyst was pressed and sieved to 18–30 mesh.

EXAMPLE 2

Nominal Composition $VSb_9Al_6O_x$ 17.17 g $Al(NO_3)_3.0.9H_2O$ was dissolved in 300 mL of de-ionized water at room temperature. Its pH was adjusted to 8.0 by the addition of 30 wt. % $NH_4OH$ to obtain white gel. 15.4 g $SbCl_3$ was placed in 150 mL of de-ionized water and stirred vigorously for 30 minutes to obtain milky-white suspension. To this suspension, 0.877 g $NH_4VO_3$ dissolved at 80° C. in 50 mL of water was added to obtain pale-yellow suspension. It was heated to 80° C., and greenish-white suspension was obtained. Upon cooling, 30% $NH_4OH$ was added dropwise to the vigorously stirred suspension, and pH was adjusted to 8.0. The resultant brown-green suspension was added to the previously prepared aluminum gel at a pH of 8.0 and stirred for an hour. The precipitate was filtered and squeezed into a light gray-green cake. The paste-like material was transferred to a porcelain dish, dried and calcined in air under the following conditions: room temperature to 120° C. at 5° C./min, held for 5 hours; 430° C. at 20° C./min, held for 4 hours; 650° C. at 20° C./min, held for 6.5 hours. The calcined material was cooled down to room temperature, ground to fine powder, pressed and sieved to 18–30 mesh.

EXAMPLE 3
Nominal Composition $VSb_5Mg_5O_x$ 1.486 g $NH_4VO_3$ was dissolved in 45 mL of de-ionized water at 80° C. Meanwhile, 14.5 g $SbCl_3$ was dissolved in 30 mL diluted nitric acid with a $HNO_1$ to $H_2O$ volume ratio of 1:3. The $SbCl_3$ solution was added to the 80° C. $NH_4VO_3$ solution, and the heat was turned off. The mixture was stirred for 30 min. 30% $NH_4OH$ was added dropwise until a pH of 8 was obtained. 16.27 g of $Mg(NO_3)_2 \cdot 6H_2O$ was dissolved in 267 mL of de-ionized water, and 30% $NH_4OH$ was added dropwise to adjust pH to 10. Then this solution was mixed with the solution containing antimony and vanadium compounds, and the resulting mixture was stirred for 1 hour. The solid was filtered, washed with 200 mL of de-ionized water and calcined in a muffle furnace with flowing air. The temperature was increased at 5° C./min to 120° C. and held at this temperature for 5 hours. It was then heated at 20° C./min to 427° C. and held at this temperature for 4 hours. The temperature was further increased at 20° C./min to 650° C. and held at this temperature for 4.5 hours. The catalyst was pressed and sieved to 18–30 mesh.

EXAMPLE 4
Nominal Composition $VSb_9Hf_6O_x$ 31.3 g $HfOCl_2 \cdot 8H_2O$ was placed in 200 mL of de-ionized water to form a solution. 26.1 g $SbCl_3$ was added to this solution. 1.50 g $NH_4VO_3$ was dissolved in 100 mL of de-ionized water at 75° C. to form a second solution. This solution was poured into the first solution containing hafnium and antimony compounds. With de-ionized water, 130 mL of 30% $NH_4OH$ was diluted to a final volume of 200 mL. The V, Sb and Hf solution was added dropwise to the aqueous ammonia solution at room temperature. The solution was filtered, and the solid was transferred to a beaker and washed with 500 mL of de-ionized water. It was filtered again. The solid was dried at 120° C. for 12 hours and crushed. It was then heated in a muffle furnace with flowing air to 800° C. at 0.9° C./min and held at this temperature for 3 hours. The calcined catalyst was pressed and sieved to 18–30 mesh.

EXAMPLE 5
Nominal Composition $VSb_9Nb_6O_x$

Dry air was flowed through a 3-neck flask equipped with an addition funnel and a magnetic stir bar. Into the addition funnel was placed 300 mL of 99.5% ethanol. 20.51 g of $NbCl_5$ was added to the 3-neck flask. The ethanol was added dropwise to the $NbCl_5$. 14.5 mL of $SbCl_5$ was injected via syringe into the addition funnel. The $SbCl_5$ was then added dropwise to the solution in the flask. After the $SbCl_5$ addition, 3.36 g of vanadyl acetylacetonate was added to the ethanol solution. 71.0 g of ammonium acetate was placed in a beaker and de-ionized water was added to give a total volume of 500 mL. The VSbNb solution was added to the ammonium acetate solution dropwise. The pH was maintained between 6 and 7.5 by the dropwise addition of 30% $NH_4OH$. The solution was filtered, and the solid was transferred to a beaker and washed with 500 mL of de-ionized water. After another filtration, the solid was dried at 120° C. for 12 hours, crushed and heated in a muffle furnace with flowing air to 800° C. at 0.9° C./min. After holding at this temperature for 3 hours, the catalyst was pressed and sieved to 18–30 mesh.

EXAMPLE 6
Nominal Composition $VSb_9Ti_6O_x$

Under vigorous stirring, 8.68 g $TiCl_4$ was added in 300 mL of de-ionized water at room temperature via dropping funnel. An exothermic reaction occurred, and a white precipitate was formed. After addition of $TiCl_4$, pH was adjusted to 9.0 with 30% $NH_4OH$ to obtain white slurry. 15.4 g $SbCl_3$ was dissolved in 30 mL diluted nitric acid with a $HNO_3$ to $H_2O$ volume ratio of 1:3 to obtain syrupy slurry. This slurry was added to the pale-yellow solution of 0.877 g $NH_4VO_3$ in 50 mL of de-ionized water at 90° C. The heat under the suspension was turned off, and the slurry was stirred for 30 minutes. The pH of the greenish-white slurry was adjusted to 8.5 with 30% $NH_4OH$. This alkaline slurry was then added to the above-prepared slurry of $TiCl_4$ and stirred for an hour. The precipitate was filtered and transferred to a porcelain dish, dried and calcined in air under the following ramp conditions: room temperature to 120° C. at 5° C./min, held for 5 hours; 430° C. at 20° C./min, held for 4 hours; 650° C. at 20° C./min, held for 6.5 hours. The calcined material was cooled down to room temperature, ground to fine powder, pressed and sieved to 18–30 mesh.

EXAMPLE 7
Nominal Composition $VSb_9Si_6O_x$ 9.53 g $Si(OC_2H_5)_4$ was added dropwise in 270 mL of deionized water at room temperature to give a suspension. After stirring 15 minutes, 30% $NH_4OH$ was added to this suspension to adjust its pH to 8.5. 0.877 g $NH_4VO_3$ was dissolved in 45 mL of deionized water at 90° C. to obtain light yellow solution. 15.4 g $SbCl_3$ was dissolved in 30 mL of diluted nitric acid (a $HNO_3$ to $H_2O$ volume ratio of 1:3) and stirred vigorously for 10 minutes to obtain yellow syrup. This syrup was added to the ammonium vanadate solution at 80° C., and a greenish-white precipitate was formed. The pH of this precipitate was adjusted to 8.5 by adding 30% $NH_4OH$ and stirred for 30 minutes. Thus obtained slurry was added to the alkaline solution of $Si(OC_2H_5)_4$ prepared above. Under constant stirring, the precipitate was dried over hot plate into a gray solid and transferred to a porcelain dish for drying and calcination. The dish with material was heated in air under the following conditions: room temperature to 120° C. at 5° C./min, held for 5 hours; 430° C. at 15° C./min, held at this temperature for 4 hours; 650° C. at 20° C./min, held for 4.5 hours at 650° C. After cooling down to room temperature, mixed metal oxide material was ground to fine powder, pressed and sieved to 18–30 mesh.

EXAMPLE 8
Nominal Composition $VSb_9Al_6Nb_8O_x$ 17.17 g $Al(NO_3)_3 \cdot 9H_2O$ was dissolved in 300 mL of de-ionized water at room temperature, and pH was adjusted to 8.5. A white gel was obtained. 15.4 g $SbCl_3$ was dissolved in 30 mL of diluted nitric acid (a $HNO_3$ to $H_2O$ volume ratio of 1:3) to obtain a syrupy slurry. This slurry was added to a pale-yellow solution of 0.877 g $NH_4VO_3$ in 50 mL of water at 90° C. to form a suspension. The heat under this suspension was turned off, and 16.2 g of $NbCl_5$ dissolved in 25 ml of concentrated HCl was added to the solution containing the antimony and vanadium compounds. After stirring for 30 minutes, the pH of the thus obtained greenish-white slurry was adjusted to 8.5 with 30% $NH_4OH$. This alkaline slurry was then added to the above-prepared alumina gel and stirred for an hour. The precipitate was filtered, transferred to a porcelain dish and heated in air under the following conditions: room temperature to 120° C. at 5° C./min, held for 5 hours; 430° C. at 20° C./min, held for 4 hours; 650° C. at 20° C./min, held for 6.5 hours. The resultant solid was cooled down to room temperature, ground to fine powder, pressed and sieved to 18–30 mesh.

EXAMPLE 9
Nominal Composition $VSb_9Al_6Mg_{0.2}O_x$ 17.17 g $Al(NO_3)_3.9H_2O$ was dissolved in 300 mL of de-ionized water. Under constant stirring, 30% $NH_4OH$ was added to obtain a gelatinous precipitate with a pH of 8. Separately, 0.877 g $NH_4VO_3$ was dissolved in 45 mL water at 85° C. and then added to a slurry prepared by dissolving 15.4 g $SbCl_3$ in 150 mL water. A solution of 0.385 g $Mg(NO_3)_2.6H_2O$ in 5 mL water was added to this mixture, and pH was adjusted to 8.0 with 30% solution of $NH_4OH$ to obtain a metallic gray precipitate. This precipitate was added to the previously prepared alumina gel, homogenized by stirring for an hour and filtered to a cake. The precipitate was dried and calcined in air under the following ramp conditions: room temperature to 120° C. at 5° C./min, held for 5 hours; 430° C. at 20° C./min, held for 4 hours; 650° at 20° C./min, held for 4.5 hours. The calcined oxide material was cooled down to room temperature, ground to fine powder, pressed and sieved to 18–30 mesh.

Comparative Example 1 and Examples 2–8 were tested for the ammoxidation of propane in a ¼ inch I.D. silica-coated stainless steel, fixed bed reactor at atmospheric pressure, 500° C. and flow rate 50 mL/min. The feed consisted of 18% $C_3H_8$, 8% $NH_3$, 14% $O_2$ and balance He. Reaction products were analyzed by on-line gas chromatography. The results are shown in Table 1 below, where AN denotes acrylonitrile.

TABLE 1

| Example | Contact Time (s) | % $C_3H_8$ Conversion | % Selectivity | | | | |
|---|---|---|---|---|---|---|---|
| | | | $C_3H_6$ | AN | $CH_3CN$ | HCN | $CO_x$ |
| Comparative 1 | 0.6 | 5 | 22 | 34 | 4 | 14 | 26 |
| 1 | 1.8 | 18 | 6 | 38 | 3 | 12 | 41 |
| 2 | 0.6 | 8 | 7 | 56 | 3 | 11 | 22 |
| 3 | 0.6 | 16 | 9 | 43 | 2 | 16 | 31 |
| 4 | 0.6 | 7 | 33 | 30 | 3 | 15 | 20 |
| 5 | 0.6 | 14 | 31 | 23 | 4 | 17 | 24 |
| 6 | 0.6 | 9 | 5 | 51 | 2 | 12 | 30 |
| 7 | 0.6 | 16 | 8 | 55 | 3 | 12 | 22 |
| 8 | 0.6 | 9 | 4 | 62 | 3 | 11 | 20 |
| 9 | 4.8 | 8.1 | 15.6 | 42.5 | 4.3 | 14.1 | 22.4 |

COMPARATIVE EXAMPLE 10
Nominal Composition $VSb_5O_x$ 34 mL of $HNO_3$ was diluted with de-ionized water to a total volume of 422 mL. To this mixture was added 28.94 g $SbCl_3$. 2.99 g $NH_4VO_3$ was placed in 100 mL of de-ionized water and heated to 75° C. This solution was poured into the $SbCl_3$ solution, and 422 g of urea was added. The resultant solution was boiled for 6 hours to obtain a gel. When boiling, de-ionized water was added periodically to maintain a constant volume. The solution was filtered, and the solid was transferred to a beaker and washed with 500 mL of de-ionized water. It was filtered again. The solid was dried at 120° C. overnight, crushed and then heated to 600° C. in flowing air at 0.9° C./min. The temperature was held at 600° C. for 3 hours. The catalyst was pressed and sieved to 18–30 mesh.

EXAMPLE 11
Nominal Composition $VSb_5Zr_5O_x$ 100 g of zirconyl nitrate hydrate was mixed with 80 mL of concentrated nitric acid. Half an hour later, the solution was diluted with de-ionized water to give a total volume of 1 L. After sitting overnight, the undissolved solid was separated from the liquid and discarded. 57.87 g of $SbCl_3$ was added to 844 mL of the zirconyl nitrate solution. To 200 mL of de-ionized water, 5.94 g $NH_4VO_3$ was added and heated to 75° C. This hot solution was then mixed with the solution containing antimony and zirconium compounds, followed by addition of 844 g urea. The solution was boiled for 6 hours to obtain a gel (periodically de-ionized water was added to maintain a constant volume). After filtration, the solid was transferred to a beaker, washed with 500 mL of water and filtered again. The solid was dried at 120° C. overnight, crushed and then heated in a muffle furnace to 600° C. in flowing air at 0.9° C./min. After calcination at 600° C. for 3 hours in air, catalyst was cooled down to room temperature, pressed and sieved to 18–30 mesh.

Comparative Example 10 and Example 11 were tested for the ammoxidation of propane in a ¼ inch I.D. silica-coated stainless steel fixed bed reactor at atmospheric pressure, 500° C. and contact time 1.2 s. The 50 mL/min feed consisted of 18% $C_3H_8$, 8% $NH_3$, 14% $O_2$ and with the balance being He. Products were analyzed by on-line gas chromatography. The conversion and selectivity of Comparative Example 10 was found to vary with time on stream (TOS). Unlike $VSb_5O_x$ in Comparative Example 10, the $VSb_5Zr_5O_x$ of Example 11 showed no change in activity and selectivity for up to 200 minutes of run under the same reaction conditions. The $C_3H_8$ conversion was 18%. The selectivities were 18% $C_3H_6$, 35% AN, 2% $CH_3CN$, 4% HCN and 42% $CO_x$. Results for these catalysts are given in Table 2 below.

TABLE 2

| Examples | TOS (min) | % $C_3H_8$ Conversion | % Selectivity | | | | |
|---|---|---|---|---|---|---|---|
| | | | $C_3H_6$ | AN | $CH_3CN$ | HCN | $CO_x$ |
| Comparative Example 10 | 25 | 5 | 22 | 28 | 2 | 14 | 33 |
| | 83 | 11 | 21 | 20 | 2 | 11 | 46 |
| | 115 | 14 | 22 | 17 | 2 | 11 | 48 |
| | 146 | 16 | 22 | 15 | 2 | 11 | 50 |
| | 178 | 18 | 23 | 13 | 2 | 11 | 52 |
| | 210 | 19 | 23 | 12 | 1 | 10 | 53 |
| Example 11 | 200 | 18 | 18 | 35 | 2 | 4 | 42 |

COMPARATIVE EXAMPLE 12
Nominal Composition $VSb_{7.5}O_x$ 34 mL of $HNO_3$ was diluted with de-ionized water to give a final volume of 422 mL. To this mixture was added 43.42 g $SbCl_3$.2.98 g $NH_4VO_3$ was placed in 100 mL of de-ionized water and heated to 75° C. This solution was poured into the $SbCl_3$ solution, and 422 g of urea was added to the mixture, which was then boiled for 6 hours to obtain a gel. De-ionized water was added periodically to maintain a constant volume.

The solution was filtered. The solid was transferred to a beaker and washed with 500 mL de-ionized water. It was filtered again. The solid was dried at 120° C. overnight, crushed, heated in a muffle furnace with flowing air to 800° C. at 0.9° C./min and calcined at this temperature for 3 hours. The finished catalyst was pressed and sieved to 18–30 mesh.

EXAMPLE 13

Nominal Composition $VSb_{7.5}Zr_{7.5}O_x$ 100 g of zirconyl nitrate hydrate was mixed with 80 mL of concentrated nitric acid. Thirty minutes later, the solution was diluted with de-ionized water to give a total volume of 1 L. After sitting overnight, the undissolved solid was separated from the liquid and discarded. 29 g of $SbCl_3$ was added to 422 mL of the zirconyl nitrate solution. To 100 mL of de-ionized water was added 1.98 g $NH_4VO_1$ and heated at 75° C. This hot solution was then added to the antimony and zirconium mixture followed by 422 g urea. The resultant solution was boiled for 6 hours to obtain a gel with de-ionized water being added periodically to maintain a constant volume. The solid was separated by filtration, transferred to a beaker, washed with 500 mL de-ionized water and filtered again. The solid was dried at 120° C. overnight, crushed, heated in a muffle furnace to 800° C. in flowing air at 0.9° C./min and held at this temperature for 3 hours. The calcined solid was pressed and sieved to 18–30 mesh.

Comparative Example 12 and Example 13 were tested for the ammoxidation of propane in a ¼ inch I.D. silica-coated stainless steel fixed bed reactor at atmospheric pressure, 475° C. and flow rate 50 mL/min. The feed consisted of 18% $C_3H_8$, 8% $NH_3$, 14% $O_2$ and balance He. Reaction products were analyzed by on-line gas chromatography. Results of these runs are presented in Table 3.

TABLE 3

| Example | Contact time (s) | % $C_3H_8$ Conversion | % Selectivity | | | | |
|---|---|---|---|---|---|---|---|
| | | | $C_3H_6$ | AN | $CH_3CN$ | HCN | $CO_x$ |
| Comp. 12 | 2.4 | 12 | 11 | 36 | 5 | 14 | 34 |
| 13 | 1.2 | 13 | 16 | 42 | 3 | 12 | 27 |

EXAMPLE 14

Nominal Composition $VSb_5Zr_5O_x$ Co-precipitated by Ammonium Hydroxide 100 g of zirconyl nitrate hydrate was mixed with 80 mL of concentrated nitric acid. Thirty minutes later, the solution was diluted with de-ionized water to give a total volume of 1 L. After sitting overnight, the undissolved solid was separated from the liquid and discarded. 14.47 g of $SbCl_3$ was added to 211 mL of the zirconyl nitrate solution. 1.49 g $NH_4VO_3$ was dissolved in 100 mL of de-ionized water, heated to 75° C. and added to the solution containing antimony and zirconium compounds. 130 mL of 30% $NH_4OH$ was diluted with de-ionized water to a total volume of 200 mL. The VSbZr solution was added dropwise to the $NH_4OH$ solution resulting in the formation of a precipitate. After filtration, the solid was transferred to a beaker, washed with 500 mL de-ionized water and filtered again. The solid was dried at 120° C. overnight and crushed, then heated in a muffle furnace to 800° C. in flowing air at 0.9° C./min and held at 800° C. for 3 hours. The calcined catalyst was pressed and sieved to 18–30 mesh.

EXAMPLE 15

Nominal Composition $VSb_5Zr_5O_x$ Co-precipitated by Urea 100 g zirconyl nitrate hydrate was mixed with 80 mL of concentrated nitric acid. Half an hour later, the solution was diluted with de-ionized water to give a total volume of 1 L. After sitting overnight, the undissolved solid was separated from the liquid and discarded. 32.3 g $SbCl_3$ was added to 476 mL of the zirconyl nitrate solution. 3.34 g $NH_4VO_3$ was dissolved in 150 mL of de-ionized water, heated at 80° C. and added to the antimony and zirconium mixture. To this solution, 476 g urea was added and boiled for 6 hours to form a gel. When boiling, de-ionized water was added periodically to maintain a constant volume. The solution was filtered, and the solid was transferred to a beaker and washed with 1 L of de-ionized water. It was filtered again. The solid was dried at 120° C. for 16 h, crushed and heated in a muffle furnace to 800° C. in flowing air at 0.9° C./min. The temperature was held at 800° C. for 3 hours. The calcined catalyst was pressed and sieved to 18–30 mesh.

EXAMPLE 16

Nominal Composition $VSb_5Zr_5Nb_2O_x$ 100 g of zirconyl nitrate hydrate was mixed with 80 mL of concentrated nitric acid. Thirty minutes later, the solution was diluted with de-ionized water to give a total volume of 1 L. After sitting overnight, the undissolved solid was separated from the liquid and discarded. 14.5 g of $SbCl_3$ was added to 211 mL of the zirconyl nitrate solution. 1.48 g $NH_4VO_3$ was dissolved in 100 mL of de-ionized water at 75° C. and added to the solution containing antimony and zirconium compounds. Then it was mixed with a warm solution containing 6.86 g of $NbCl_5$ in 40 mL of water, and 211 g of urea was added to the mixture. The resultant solution was boiled for 6 hours to obtain a gel, periodically adding de-ionized water to maintain a constant volume. After filtration, the solid was dried at 120° C. overnight, crushed and heated in a muffle furnace to 800° C. in flowing air at 0.9° C./min. The catalyst was held at 800° C. for 3 hours, cooled down, and then pressed and sieved to 18–30 mesh.

EXAMPLE 17

Nominal Composition $VSb_5Zr_5Mg_{0.3}O_x$ 100 g of zirconyl nitrate hydrate was mixed with 80 mL of concentrated nitric acid. Thirty minutes later, the solution was diluted with de-ionized water to give a total volume of 1 L. After sitting overnight, the undissolved solid was separated from the liquid and discarded. 28.95 g of $SbCl_3$ was added to 422 mL of the zirconyl nitrate solution. 2.98 g $NH_4VO_3$ was dissolved in 100 mL of water and heated at 75° C. 1.974 g $Mg(NO_3)_2 \cdot 6H_2O$ was dissolved in 5 mL water and added to the $NH_4VO_3$ solution. The resulting mixture was added to the solution containing zirconium and antimony compounds, followed by adding 422 g urea. The solution was boiled for 6 h to obtain a gel, periodically adding de-ionized water to maintain a constant volume. The solution was filtered, and the solid was transferred to a beaker, washed with de-ionized water and filtered again. The solid was dried at 120° C. overnight, crushed and heated in a muffle furnace to 800° C. in flowing air at 0.9° C./min. The temperature was held at 800° C. for 3 hours. The calcined catalyst was pressed and sieved to 18–30 mesh.

EXAMPLES 18–30

Nominal Compositions $VSb_5Zr_5Q_cO_x$ Prepared by Co-precipitation Where Q=P (18), Y (19), La (20), W (21), Mo (22), Ce (23), Bi (24), Na (25), Mn (26), Ga (27), Cr (28), Zn (29), and Ag (30)

100 g of zirconyl nitrate hydrate was mixed with 80 ML of concentrated nitric acid. Thirty minutes later, the solution was diluted with de-ionized water to give a total volume of 1 L. After sitting overnight, the undissolved solid was separated from the liquid and discarded. 14.5 g of $SbCl_3$ was added to 211 mL of the zirconyl nitrate solution. 1.49 g $NH_4VO_3$ was dissolved in 100 mL of de-ionized water, heated at 75° C. and mixed with the solution containing antimony and zirconium compounds. To the resultant solution, a compound containing Q element was added. These compounds were $H_3PO_4$, $Y(NO_3)_3 \cdot 6H_2O$, $La(CH_3CO_2)_3 \cdot H_2O$, $Ce(NO_3)_3 \cdot 6H_2O$, $(NH_4)_2MoO_4$, $(NH_4)_2WO_4$, $Bi(NO_3)_3 \cdot 5H_2O$, $NaNO_3$, $Mn(NO_3)_3 \cdot 18H_2O$, $Ga(NO_3)_3 \cdot 7H_2O$, $Cr(NO_3)_3 \cdot 9H_2O$, $Zn(NO_3)_3 \cdot 6H_2O$ and $AgNO_3$. Weights of these compounds were calculated according to the element atomic ratios ($Q_c$) listed in Table 4. After that, 211 g urea was added to the mixture, and the solution was boiled for 6 h to obtain a gel. During boiling, de-ionized water was added periodically to maintain a constant volume. The solution was filtered, and the solid was transferred to a beaker and washed with 750 mL de-ionized water. It was filtered again, and the solid was dried at 120° C. overnight, crushed and heated to 800° C. in flowing air at 0.9° C./min. The solid was calcined at 800° C. for 3 hours, cooled down, pressed and sieved to 18–30 mesh.

EXAMPLE 31
Nominal Composition $VSb_5Zr_5Mo_{0.05}O_x$ Prepared by Impregnation 100 g of zirconyl nitrate hydrate was mixed with 80 mL of concentrated nitric acid. Thirty minutes later, the solution was diluted with de-ionized water to give a total volume of 1 L. After sitting overnight, the undissolved solid was separated from the liquid and discarded. 43.4 g of $SbCl_3$ was added to 633 mL of the zirconyl nitrate solution. 4.46 g $NH_4VO_3$ was dissolved in 100 mL of de-ionized water, heated at 75° C. and added to the solution containing antimony and zirconium compounds. To this mixed solution, 633 g urea was added and boiled for 5 hours to obtain a gel, periodically adding de-ionized water to maintain a constant volume. The solution was filtered, and the solid was transferred to a beaker and washed with 500 mL of de-ionized water. It was filtered again, and the solid was dried at 120° C. overnight and crushed. 0.296 g $(NH_4)_2Mo_2O_{24} \cdot 4H_2O$ was dissolved in 45 mL of de-ionized water. The solution was poured on 49.39 g of the VSbZr dried solid, and the liquid was evaporated off. The impregnated solid was dried at 120° C. overnight and then heated to 800° C. in flowing air at 0.9° C./min. After calcining at 800° C. for 3 hours, the catalyst was pressed and sieved to 18–30 mesh.

EXAMPLE 32
Nominal Composition $VSb_5Zr_5P_{0.1}O_x$ Prepared by Impregnation 100 g of zirconyl nitrate hydrate was mixed with 80 mL of concentrated nitric acid. Half an hour later, the solution was diluted with de-ionized water to give a total volume of 1 L. After sitting overnight, the undissolved solid was separated from the liquid and discarded. 43.4 g of $SbCl_3$ was added to 633 mL of the zirconyl nitrate solution. 4.46 g $NH_4VO_3$ was dissolved in 100 mL of de-ionized water, heated at 75° C. and added to the solution containing antimony and zirconium compounds. To this mixture, 633 g urea was added, and the resultant solution was boiled for 6 hours to obtain a gel. De-ionized water was added periodically to maintain a constant volume. The suspension was filtered, and the solid was transferred to a beaker, washed with 750 mL of de-ionized water and filtered again. The solid was dried at 120° C. overnight and crushed. 0.466 g of $(NH_4)H_2PO_4$ was dissolved in 100 mL of hot de-ionized water and poured on 54.93 g of the above-prepared VSbZr dried solid. The liquid was evaporated off, and the impregnated solid was dried at 120° C. overnight, crushed and heated to 800° C. in flowing air at 0.9° C./min. The catalyst was held at 800° C. for 3 hours, cooled down, pressed and sieved to 18–30 mesh.

EXAMPLE 33
Nominal Composition $VSb_5Zr_5W_{0.05}O_x$ Prepared by Impregnation 100 g of zirconyl nitrate hydrate was mixed with 80 mL of concentrated nitric acid. Half an hour later, the solution was diluted with de-ionized water to give a total volume of 1L. After sitting overnight, the undissolved solid was separated from the liquid and discarded. 32.3 g of $SbCl_3$ was added to 476 mL of the zirconyl nitrate solution. 3.34 g $NH_4VO_3$ was dissolved in 100 mL of de-ionized water, heated at 75° C. and mixed with the solution containing antimony and zirconium compounds. To this mixture, 476 g urea was added and boiled for 6 hours to obtain a gel. De-ionized water was added periodically to maintain a constant volume. The suspension was filtered, and the solid was transferred to a beaker and washed with 1 L of de-ionized water. It was filtered again, and the solid was dried at 120° C. overnight and crushed. 0.346 g ammonium paratungstate was dissolved in 70 mL of heated de-ionized water. The solution was poured onto 39.5 g of the above-prepared VSbZr dried solid, and the liquid was evaporated off. The impregnated solid was dried at 120° C. overnight, heated in a muffle furnace to 800° C. in flowing air at 0.9° C. and held at 800° C. for 3 hours. The calcined catalyst was pressed and sieved to 18–30 mesh.

Examples 14–33 were tested for the ammoxidation of propane in a ¼ inch I.D. silica-coated stainless steel fixed bed reactor at atmospheric pressure, 475° C. and flow rate 50 mL/min. The feed consisted of 18% $C_3H_8$, 8% $NH_3$, 14% $O_2$ and balance He. Reaction products were analyzed by on-line gas chromatography. The results of these runs are presented in Table 4.

TABLE 4

| Example | $Q_c$ | Contact time (s) | % $C_3H_8$ Conversion | % Selectivity | | | | |
|---|---|---|---|---|---|---|---|---|
| | | | | $C_3H_6$ | AN | $CH_3CN$ | HCN | $CO_x$ |
| 14 | None | 1.2 | 10 | 16 | 36 | 4 | 12 | 31 |
| 15 | None | 1.2 | 19 | 9 | 43 | 2 | 19 | 27 |
| 16 | None | 0.36 | 14 | 26 | 30 | 5 | 15 | 24 |
| 17 | none | 0.24 | 12 | 28 | 30 | 4 | 14 | 24 |
| 18 | $P_4$ | 1.2 | 11 | 35 | 33 | 4 | 13 | 16 |
| 19 | $Y_1$ | 1.2 | 16 | 24 | 33 | 3 | 13 | 28 |
| 20 | $La_{0.3}$ | 0.6 | 17 | 25 | 30 | 3 | 14 | 29 |
| 21 | $W_{0.3}$ | 1.2 | 27 | 20 | 25 | 4 | 14 | 37 |
| 22 | $Mo_{0.3}$ | 1.2 | 14 | 30 | 19 | 6 | 16 | 29 |
| 23 | $Ce_{0.3}$ | 1.2 | 16 | 18 | 36 | 1 | 12 | 33 |
| 24 | $Bi_1$ | 1.2 | 20 | 22 | 31 | 2 | 10 | 35 |
| 25 | $Na_{0.3}$ | 1.2 | 12 | 28 | 34 | 3 | 11 | 25 |
| 26 | $Mn_1$ | 0.6 | 9 | 30 | 32 | 3 | 11 | 23 |
| 27 | $Ga_{0.3}$ | 1.2 | 16 | 17 | 42 | 3 | 11 | 28 |
| 28 | $Cr_1$ | 0.36 | 13 | 16 | 39 | 3 | 13 | 28 |
| 29 | $Zn_{0.3}$ | 0.6 | 14 | 15 | 41 | 3 | 14 | 28 |
| 30 | $Ag_{0.3}$ | 1.2 | 10 | 26 | 30 | 3 | 8 | 34 |
| 31 | $Mo_{0.05}$ | 1.2 | 5 | 47 | 22 | 4 | 9 | 18 |
| 32 | $P_{0.1}$ | 1.2 | 11 | 32 | 33 | 4 | 15 | 16 |
| 33 | $W_{0.05}$ | 1.2 | 17 | 12 | 42 | 3 | 19 | 24 |

EXAMPLE 34
Nominal Composition $VSb_9Al_6K_2O_x$ Prepared by Co-precipitation 17 g of $Al(NO_3)_3 \cdot 9H_2O$ was dissolved in 300 mL of de-ionized water. Under constant stirring, 30% $NH_4OH$ was added until a pH was 8.0 obtained. A gelatinous precipitate resulted. Separately, 0.877 g of $NH_4VO_3$ was dissolved in 45 mL of de-ionized water at 85° C. and added to the slurry of 15.4 g of $SbCl_3$ in 150 mL of de-ionized water. To this mixture, a solution of 0.96 g of KOH (13 wt. % $H_2O$) in 5 mL of water was added, and the pH of resultant slurry was adjusted to 8.0 with 30% solution of $NH_4OH$ to obtain metallic gray precipitate. Under stirring, this precipitate was added to the previously prepared alumina slurry to obtain homogenized mixture. After stirring for an hour, it was filtered to a cake that was dried and calcined in air under the following conditions: room temperature to 120° C. at 5° C./min, held for 5 hours; 430° C. at 20° C./min, held for 4 hours; 650° C. at 20° C./min, held for 4.5 hours. The mixed metal oxide material thus prepared was cooled down to room temperature, ground to fine powder, pressed and sieved to 18–30 mesh.

EXAMPLES 35 to 46
Nominal Compositions $VSb_9Al_6Q_cO_x$ Prepared by Co-precipitation Where Q=Ca (35), Sr (36), Ba (37), B (38), P (39), Y (40), Zn (41), W (42), Cu (43), Mn (44), Mo (45), Ce (46)

The atomic ratios of these elements in catalysts denoted as $Q_c$ are given in Table 7. The following catalysts were synthesized according to Example 34, excepting that KOH was replaced by the corresponding metal salt dissolved in 5 to 10 mL of de-ionized water. The metal salts used for catalyst preparation are listed in Table 5.

TABLE 5

| Example | Metal salt | Weight (gm) | Final color of slurry |
|---|---|---|---|
| 34 | $Ca(NO_3)_2 \cdot 4H_2O$ | 0.355 | Gray |
| 36 | $Sr(NO_3)_2$ | 0.317 | Grayish-green |
| 37 | $Ba(NO_3)_2$ | 0.393 | Greenish-gray |
| 38 | $H_3BO_3$ | 0.232 | Gray |
| 39 | 85% $H_3PO_4$ | 0.422 | Dark gray |
| 40 | $Y(NO_3)_3 \cdot 6H_2O$ | 0.722 | Grayish brown |
| 41 | $Zn(NO_3)_2 \cdot 6H_2O$ | 0.680 | Metallic gray |
| 42 | $(NH_4)_{10}W_{12}O_{42}$ | 1.911 | Grayish green |
| 43 | $Cu(NO_3)_2 \cdot 6H_2O$ | 0.665 | Grayish green |
| 44 | $Mn(NO_3)_2 \cdot 18H_2O$ | 1.885 | Grayish green |
| 45 | $(NH_4)_2MoO_4$ | 0.490 | Grayish green |
| 46 | $Ce(NO_3)_3 \cdot 6H_2O$ | 0.976 | Light brown |

EXAMPLE 47
Nominal Composition $VSb_9Al_6Ta_1O_x$ Prepared by Co-precipitation 17.17 g $Al(NO_3)_3 \cdot 9H_2O$ was dissolved in 270 mL of de-ionized water at room temperature, and pH was adjusted to 8.0 with 30% $NH_4OH$. A white gel was obtained. 15.4 g $SbCl_3$ was placed in 150 mL of de-ionized water and stirred vigorously for 30 minutes to obtain a milky-white suspension. Under stirring, 2.68 g of solid $TaCl_5$ was added to the antimony chloride suspension. To the resultant suspension, 0.877 g of $NH_4VO_3$ dissolved at 80° C. in 50 mL of water was added while heating to 80° C. to obtain pale-yellow precipitate. A greenish-white suspension was obtained. The heat was turned off and under vigorous stirring, 30% $NH_4OH$ was added dropwise to adjust pH to 8.0. A light brown suspension was obtained. This material was then added to the previously prepared aluminum gel at a pH of 8.0 and stirred for an hour. The precipitate was filtered and squeezed to a cake. The paste-like material was dried and calcined in static airflow under the following conditions: room temperature to 120° C. at 5° C./min, held for 5 hours; 430° C. at 20° C./min, held for 4 hours; 650° C. at 20° C./min, held for 4.5 hours. The calcined material was ground to a fine powder, pressed and sieved to 18–30 mesh.

EXAMPLE 48
Nominal Composition $VSb_9Al_6Re_{2.3}O_x$ Prepared by Co-precipitation 17.2 g $Al(NO_3)_3 \cdot 9H_2O$ was dissolved in 270 mL of de-ionized water at room temperature, and pH was adjusted to 8.0 with 30% $NH_4OH$ to obtain white gel. 15.4 g $SbCl_3$ was immersed in 150 mL of de-ionized water and stirred vigorously for 30 minutes to obtain milky-white suspension. Under stirring, 4.53 g of solid $NH_4ReO_4$ and 0.877 g of $NHVO_3$ were dissolved at 80° C. in 75 mL of de-ionized water to obtain pale-yellow solution. This solution was added to the antimony chloride slurry at room temperature and heated to 80° C. to obtain a green-yellow suspension. The heat was turned off, and under vigorous stirring, 30% $NH_4OH$ was added dropwise to adjust pH to 8.0. Light cherry suspension was obtained that was added to previously prepared aluminum gel at a pH of 8.0 and stirred for an hour. The precipitate was filtered and squeezed to a cake. The paste-like material was dried and calcined in air under the following conditions: room temperature to 120° C. at 5° C./min, held for 5 hours; 430° C. at 20° C./min, held for 4 hours; 650° C. at 20° C./min, held for 6.5 hours. The calcined catalyst was ground to a fine powder, pressed and sieved to 18–30 mesh.

EXAMPLE 49
Nominal Composition $VSb_9Al_6Ga_2O_x$ Prepared by Co-precipitation 17.2 g $Al(NO_3)_3 \cdot 9H_2O$ was dissolved in 267 mL of de-ionized water at room temperature, and pH was adjusted to 8.0 with 30% NH4OH to obtain white gel. 15.4 g $SbCl_3$ was dissolved in 30 mL of diluted nitric acid (a $HNO_3$ to $H_2O$ volume ratio of 1:3) and stirred vigorously for 30 minutes to obtain milky-white suspension. Under stirring, 0.877 g of $NH_4VO_3$ was dissolved in 45 mL of de-ionized water at 80° C. to obtain yellow solution. The antimony chloride suspension was then added to the ammonium vanadate solution. This suspension was combined solution was then mixed at 80° C. with a clear solution of 4.28 g of $Ga(NO_3)_3 \cdot 7H_2O$ in 24 mL of diluted nitric acid (a $HNO_3$ to $H_2O$ volume ratio of 1:3). The heat was turned off, and after stirring for 30 minutes, 30% $NH_4OH$ was added dropwise to adjust pH to 8.0. The resultant suspended material was then added to previously prepared aluminum gel at a pH of 8.0 and stirred for an hour. The precipitate was filtered and squeezed to a cake, which was dried and heated in air under the following conditions: room temperature to 120° C. at 5° C./min, held for 5 hours; 430° C. at 20° C./min, held for 4 hours; 650° C. at 20° C./min, held for 6.5 hours. The calcined mixed metal oxide catalyst was ground to a fine powder, pressed and sieved to 18–30 mesh.

EXAMPLE 50 to 56
Nominal Compositions $VSb_9Al_6Q_cO_x$ Prepared by Co-precipitation Where Q=In (50), Sn (51), Fe (52), Co (53), Ni (54), Cd (55), Bi (56).

The atomic ratios of Q elements denoted as $Q_c$ are given in Table 7. These catalysts were prepared by the method described above in Example 48, except that instead of Ga(NO$_3$)$_3$.7H$_2$O the metal salts listed in Table 6 were utilized. As a solvent for them, diluted nitric acid (a HNO$_3$ to H$_2$O volume ratio of 1:3) was used.

TABLE 6

| Example | Metal salt | Weight (gm) | Solvent (mL) |
|---|---|---|---|
| 50 | In(NO$_3$)$_3$.H$_2$O | 4.78 | 24 |
| 51 | Sn(II) tartarate | 4.03 | 60 |
| 52* | Fe(NO$_3$)$_3$.9H$_2$O | 1.00 | 4 |
| 53* | Co(NO$_3$)$_2$.6H$_2$O | 0.72 | 4 |
| 54* | Ni(NO$_3$)$_2$.6H$_2$O | 4.36 | 24 |
| 55 | Cd(NO$_3$)$_2$.4H$_2$O | 4.62 | 24 |
| 56 | Bi(NO$_3$)$_3$.5H$_2$O | 1.20 | 4 |

*Filtered cake was washed with 200 mL of de-ionized water

EXAMPLES 57–60

Nominal Compositions VSb$_9$Al$_6$Q$_c$O$_x$ Prepared by Impregnation Where Q=P (57), Zn (58), B (59), and W (60)

Base oxide composition VSb$_9$Al$_6$O was prepared by method described in Example 2. The powder of this mixed metal oxide was impregnated by incipient wetness with aqueous solutions of H$_3$PO$_4$, Zn(NO$_3$)$_2$, H$_3$BO$_3$ and (NH$_4$)$_2$WO$_4$. Weights of these compounds dissolved in 7 mL of de-ionized water were calculated according to the element atomic ratios (Q$_c$) listed in Table 7. The impregnated materials were dried and calcined as per Example 2.

Examples 33–59 were tested for the ammoxidation of propane in a ¼ inch I.D. silica-coated stainless steel fixed bed reactor at atmospheric pressure, 500° C. and contact time 0.6 s. The 50 mL/min feed consisted of 18% C$_3$H$_8$, 8% NH$_3$, 14% O$_2$ and the balance being He. Reaction products were analyzed by on-line gas chromatography. The results of these runs are given in Table 7.

TABLE 7

| Example | Q$_c$ | % C$_3$H$_8$ Conversion | % Selectivity | | | |
|---|---|---|---|---|---|---|
| | | | C$_3$H$_6$ | AN | CH$_3$CN | HCN | CO$_x$ |
| 34 | K$_2$ | 6.7 | 17.9 | 37.7 | 2.2 | 8.7 | 33.5 |
| 35 | Ca$_{0.2}$ | 24.8 | 19.5 | 39.3 | 2.7 | 10.8 | 27.6 |
| 36 | Sr$_{0.2}$ | 12.7 | 3.9 | 54.6 | 2.3 | 11.6 | 27.8 |
| 37 | Ba$_{0.2}$ | 21.5 | 18.6 | 41.2 | 2.2 | 10.3 | 27.8 |
| 38 | B$_{0.5}$ | 12.9 | 4.2 | 57.4 | 3.0 | 11.8 | 23.6 |
| 39 | P$_{0.5}$ | 11.0 | 4.7 | 54.7 | 2.8 | 12.2 | 25.6 |
| 40 | Y$_{0.2}$ | 19.0 | 18.1 | 39.0 | 1.8 | 10.7 | 30.4 |
| 41 | Zn$_{0.3}$ | 8.7 | 7.3 | 58.0 | 3.2 | 11.1 | 20.4 |
| 42 | W$_1$ | 13.8 | 11.8 | 57.4 | 3.5 | 11.7 | 15.6 |
| 43* | Cu$_{0.3}$ | 17.7 | 16.9 | 40.4 | 1.9 | 8.5 | 32.3 |
| 44* | Mn$_{0.5}$ | 14.6 | 23.1 | 39.2 | 2.8 | 11.3 | 23.6 |
| 45 | Mo$_{0.3}$ | 9.7 | 7.8 | 60.7 | 3.1 | 10.6 | 17.8 |
| 46 | Ce$_{0.3}$ | 14.6 | 19.1 | 37.4 | 1.7 | 11.8 | 30.8 |
| 47 | Ta$_1$ | 20.6 | 18.0 | 40.7 | 2.6 | 11.0 | 27.7 |
| 48 | Re$_{2.3}$ | 9.1 | 5.7 | 54.0 | 3.4 | 16.8 | 18.4 |
| 49 | Ga$_2$ | 17.7 | 12.2 | 42.8 | 2.9 | 10.5 | 31.6 |
| 50 | In$_2$ | 20.9 | 16.6 | 39.4 | 2.0 | 9.7 | 32.3 |
| 51 | Sn$_2$ | 15.1 | 13.4 | 44.1 | 2.4 | 10.1 | 30.0 |
| 52 | Fe$_{0.3}$ | 12.7 | 5.7 | 47.0 | 2.4 | 12.1 | 32.7 |
| 53 | Co$_{0.3}$ | 8.3 | 8.4 | 50.9 | 3.7 | 11.4 | 25.6 |
| 54 | Ni$_2$ | 9.1 | 27.4 | 40.0 | 3.5 | 9.0 | 20.4 |
| 55 | Cd$_2$ | 24.2 | 20.8 | 37.6 | 2.7 | 10.8 | 28.2 |
| 56 | Bi$_{0.3}$ | 12.6 | 4.0 | 54.3 | 3.6 | 12.3 | 25.7 |
| 57 | P$_{0.05}$ | 9.2 | 4.1 | 56.7 | 3.8 | 13.5 | 22.0 |
| 58 | Zn$_{0.05}$ | 10.9 | 2.5 | 53.0 | 3.4 | 12.4 | 28.7 |
| 59 | B$_{0.05}$ | 8.7 | 3.5 | 56.3 | 3.8 | 13.2 | 23.4 |
| 60 | W$_{0.06}$ | 12.0 | 4.7 | 61.3 | 3.4 | 12.4 | 18.1 |

*Contact time 0.2 seconds

Examples 61–68

Nominal Compositions VSb$_9$Al$_6$W$_{0.56}$Q$_t$O$_x$ Prepared by Impregnation where Q'B (61–63), In (64), Y (65), Sc (66), Bi (67) and Ta (68)

Base oxide VSb$_9$Al$_6$O$_x$ was prepared by the method described in Example 2. 5 grams of this material were impregnated by incipient wetness with the mixed solution containing ammonium tungstate and the salt of Q element. The solution was prepared by dissolving 47.6 mg (NH$_4$)$_2$WO$_4$ in 15 mL of de-ionized water followed by adding Q precursor. The Q precursors as well as their quantities calculated according to the atomic ratios described in the Examples 61–68 are listed in Table 8. The solution was poured over base VSb$_9$Al$_6$O$_x$ and the liquid was evaporated off on a hot plate under continuous stirring. Thus impregnated solid was dried at 120° C. for 5 hours and heated in air in a muffle furnace at 430° C. for 4 hours and then at 650° C. for 4.5 hours. The heating rates were as mentioned in Example 2. The calcined catalyst was pressed and sieved to 18–30 mesh.

TABLE 8

| Example number | Q element salt | Salt weight (mg) | Solvent (mL) |
|---|---|---|---|
| 61, 62 | H$_3$BO$_3$ | 10.4 | Water (15) |
| 63 | H$_3$BO$_3$ | 41.6 | Water (15) |
| 64 | In(NO$_3$)$_3$.H$_2$O | 26.8 | Water (15) |
| 65 | Y(NO$_3$)$_3$.6H$_2$O | 32.2 | Water (15) |
| 66 | Sc(NO$_3$)$_3$.4H$_2$O | 25.5 | Water (15) |
| 67 | Bi(NO$_3$)$_3$.5H$_2$O | 81.5 | 2.0N HNO$_3$ (15) |
| 68 | TaCl$_5$ | 60.2 | Water (15) |

Examples 61–68 were tested for the ammoxidation of propane in a ¼ inch I.D. silica-coated stainless steel fixed bed reactor at atmospheric pressure, 500° C. and contact time of 0.6 seconds. The 50 mL/min feed consisted of 18% propane, 8.0% ammonia, 14% oxygen and the balance being helium. Reaction products were analyzed by on-line gas chromatography. The results of these runs are given in Table 9, where AN denotes acrylonitrile.

TABLE 9

| Example Number | Q$_c$ | % C$_3$H$_8$ Conversion | % Selectivity | | | |
|---|---|---|---|---|---|---|
| | | | C$_3$H$_6$ | AN | CH$_3$CN | HCN | CO$_x$ |
| 61 | B$_{0.06}$ | 11.1 | 5.3 | 63.4 | 3.2 | 11.9 | 16.2 |
| 62 | B$_{0.06}$* | 21.2 | 2.0 | 60.6 | 2.6 | 11.6 | 23.2 |
| 63 | B$_{0.24}$ | 11.8 | 3.8 | 62.7 | 3.2 | 12.4 | 17.8 |
| 64 | In$_{0.06}$ | 10.2 | 6.1 | 63.5 | 3.3 | 11.7 | 15.5 |
| 65 | Y$_{0.03}$ | 11.1 | 6.4 | 61.6 | 2.9 | 11.8 | 17.3 |
| 66 | Sc$_{0.03}$ | 9.9 | 5.7 | 62.6 | 3.2 | 11.2 | 17.2 |
| 67 | Bi$_{0.06}$ | 13.6 | 3.4 | 63.1 | 3.1 | 12.3 | 18.2 |
| 68 | Ta$_{0.06}$ | 9.9 | 5.7 | 62.3 | 3.6 | 11.6 | 16.8 |

*Contact time 1.6 seconds

EXAMPLE 69

Nominal Composition VSb$_{10}$Mg$_3$O$_x$ 0.88 g NH$_4$VO$_3$ was dissolved in 45 mL of de-ionized water at 80° C. Meanwhile, 10.9 g Sb$_2$O$_3$ was placed in 30 mL diluted nitric acid with a HNO$_3$ to H$_2$O volume ratio of 1:3. The NH$_4$VO$_3$ solution was added to the Sb slurry, and the mixture was stirred for 30 min without heating. 30% NH$_4$OH was added dropwise until a pH of 8 was obtained. 5.87 g of Mg(NO$_3$)$_2$.6H$_2$O was dissolved in 267 mL of de-ionized water, and 30% NH$_4$OH was added dropwise to adjust pH to 10. Then this slurry was mixed with the slurry containing antimony and vanadium compounds, and the resulting mixture was stirred for 1 hour. The mixture was heated on the hot plate until most of the solution had evaporated and a paste-like material remained. The paste-like material was dried overnight at 120° C. It was then calcined in a muffle furnace to 800° C. in flowing air at 0.9° C./min and held at 800° C. for 3 h. The catalyst was pressed and sieved to 18–30 mesh.

EXAMPLE 70
Nominal Composition $VSb_{10}Mg_3W_{2.24}O_x$ Prepared by Impregnation 0.0480 g ammonium tungstate was dissolved in 60 mL de-ionized water. The solution was poured over 5.671 g calcined $VSb_{10}Mg_3O_x$ which was prepared as in Example 68. The liquid was evaporated off on a hot plate. The impregnated solid was dried at 120° C. overnight. It was then heated in a muffle furnace to 80° C. in flowing air at 0.9° C./min and held at 800° C. for 3 hours. The calcined catalyst was pressed and sieved to 18–30 mesh.

EXAMPLES 71–75
Nominal Compositions $VSb_{10}Mg_3W_{0.04}Q_cO_x$ Prepared by Impregnation Where Q=Na (71), Cr (72), Fe (73), Ga (74) and Bi (75)

Ammonium metatungstate was dissolved in 60 mL de-ionized water followed by a Q precursor which consisted of $NaNO_3$, $Cr(NO_3)_3 \cdot 9H_2O$, $Fe(NO_3)_3 \cdot 9H_2O$, $Ga(No_3)_3 \cdot 7H_2O$, and $Bi(NO_3)_3 \cdot 5H_2O$. The solutions were poured over 120° C. dried, but not calcined $VSb_{10}Mg_3O_x$ bases prepared as in Example 68. Table 10 shows the quantities of ammonium metatungstate, Q precursor and dried $VSb_{10}Mg_3O_x$ base material used for each of the examples.

TABLE 10

| Example | Q element salt | Grams of ammonium meta-tungstate | Grams of Q precursor | Grams of dried $VSb_{10}Mg_3O_x$ |
|---|---|---|---|---|
| 71 | $NaNO_3$ | 0.101 | 0.035 | 16.18 |
| 72 | $Cr(NO_3)_3 \cdot 9H_2O$ | 0.062 | 0.100 | 10.01 |
| 73 | $Fe(NO_3)_3 \cdot 9H_2O$ | 0.102 | 0.167 | 16.65 |
| 74 | $Ga(NO_3)_3 \cdot 7H_2O$ | 0.063 | 0.098 | 10.34 |
| 75 | $Bi(NO_3)_3 \cdot 5H_2O$ | 0.068 | 0.128 | 10.49 |

Examples 69–75 were tested for the ammoxidation of propane in a ¼ inch I.D. silica-coated stainless steel fixed bed reactor at atmospheric pressure and 500° C. The 50 mL/min feed consisted of 18% $C_3H_8$, 8% $NH_3$, 14% $O_2$ and the balance being He. Reaction products were analyzed by on-line gas chromatography. The results of these runs are given in Table 11.

TABLE 11

| Example | $Q_c$ | Contact time (s) | % $C_3H_8$ Conversion | % Selectivity $C_3H_6$ | AN | $CH_3CN$ | HCN | $CO_x$ |
|---|---|---|---|---|---|---|---|---|
| 69 | None | 0.6 | 8.3 | 20.6 | 37.3 | 2.3 | 10.7 | 29.1 |
| 70 | $W_{0.04}$ | 1.2 | 11.1 | 4.4 | 54.8 | 3 | 15.7 | 22.1 |
| 71 | $Na_{0.05}W_{0.04}$ | 1.8 | 12.9 | 5.8 | 52.8 | 3.2 | 17.0 | 21.2 |
| 72 | $Cr_{0.04}W_{0.04}$ | 1.2 | 16.9 | 3.4 | 55.5 | 3.5 | 14.8 | 22.7 |
| 73 | $Fe_{0.04}W_{0.04}$ | 1.2 | 11.7 | 6.3 | 51.1 | 3.4 | 18.8 | 20.3 |
| 74 | $Ga_{0.04}W_{0.04}$ | 1.2 | 17.9 | 5.6 | 50.2 | 3.2 | 13.7 | 27.3 |
| 75 | $Bi_{0.05}W_{0.04}$ | 1.2 | 19.8 | 5.1 | 51.1 | 3.6 | 15.8 | 24.4 |

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letter of Patent of the United States of America is:

1. A catalyst composition for vapor phase ammoxidation of alkanes and olefins comprising a compound of the formula:

$$VSb_aM_bO_x$$

wherein V is vanadium, Sb is antimony, M is at least one element selected from the group consisting of magnesium, aluminum, zirconium, silicon, hafnium, titanium and niobium, a is from 0.5 to 20, b is 2 to 50 and x is determined by the valence requirements of the other elements present and wherein vanadium and antimony are isolated in a matrix of the oxides of M.

2. The catalyst composition of claim 1 wherein M is one element selected from the group consisting of magnesium, aluminum, zirconium, silicon, hafnium, titanium and niobium.

3. The catalyst composition of claim 1 wherein the formula is

$$VSb_aM_cM'_bO_x$$

wherein M and M' are each one element selected from the group consisting of magnesium, aluminum, zirconium, silicon, hafnium, titanium and niobium, M and M' are different and b' is 0 to 50.

4. The catalyst composition of claim 3 wherein M is aluminum and M' is niobium or magnesium.

5. The catalyst composition of claim 3 wherein M is zirconium and M' is niobium or magnesium.

6. The catalyst composition of claim 1 wherein the formula is

$$VSb_aM_bQ_cO_x$$

wherein Q is at least one element selected from the group consisting of rhenium, tungsten, molybdenum, tantalum, manganese, phosphorus, cerium, tin, boron, scandium, bismuth, gallium, indium, iron, chromium, lanthanum, yttrium, zinc, cobalt, nickel, cadmium, copper, strontium, barium, calcium, silver, potassium, sodium and cesium and c is 0 to 10.

7. The catalyst composition of claim 6 wherein M is aluminum and Q is potassium, calcium, strontium, barium, boron, scandium, phosphorus, yttrium, zinc, tungsten, copper, manganese, molybdenum, cerium, tantalum, rhenium, gallium, indium, tin, iron, cobalt, nickel, cadmium or bismuth.

8. The catalyst composition of claim 6 wherein M is zirconium and Q is phosphorus, yttrium, lanthanum, tungsten, molybdenum, cerium, bismuth, sodium, manganese, gallium, chromium, zinc or silver.

9. The catalyst composition of claim 6 wherein M is magnesium and Q is tungsten.

10. The catalyst composition of claim 1 wherein the formula is $$VSb_aM_bQ_cQ'_{c'}O_x$$

wherein Q and Q' are each one element selected from the group consisting of rhenium, tungsten, molybdenum, tantalum, manganese, phosphorus, cerium, tin, boron, scandium, bismuth, gallium, indium, iron, chromium, lanthanum, yttrium, zinc, cobalt, nickel, cadmium, copper, strontium, barium, calcium, silver, potassium, sodium and cesium and c' is 0 to 10.

11. The catalyst composition of claim 10 wherein M is aluminum, Q is tungsten and Q' is one element selected from the group consisting of boron, indium, yttrium, scandium, bismuth and tantalum.

12. The catalyst composition of claim 10 wherein M is magnesium and Q is tungsten and Q' is one element selected from the group consisting of sodium, chromium, iron, gallium and bismuth.

13. The catalyst composition of claim 1 wherein vanadium, antimony and M are coprecipitated.

14. The catalyst composition of claim 3 wherein vanadium, antimony, M and M' are coprecipitated.

15. The catalyst composition of claim 6 wherein vanadium, antimony, M and Q are coprecipitated.

16. The catalyst composition of claim 6 wherein vanadium, antimony and M are coprecipitated and Q is impregnated.

17. The catalyst composition of claim 10 wherein vanadium, antimony and M are coprecipitated and Q and Q' are impregnated.

18. A process of making a catalyst composition for vapor phase ammoxidation of alkanes and olefins comprising:
a) forming a solution of a vanadium compound, an antimony compound and at least one compound of M wherein M is selected from the group consisting of magnesium, aluminum, zirconium, silicon, hafnium, titanium and niobium;
b) adding and mixing a base with the solution;
c) coprecipitating hydroxides of vanadium, antimony and M;
d) separating the coprecipitated hydroxide solid from solution;
e) drying the hydroxide solid; and
f) calcining the hydroxide solid to form a catalyst of the formula:

$$VSb_aM_bO_x$$

wherein a is from 0.5 to 20, b is 2 to 50 and x is determined by the valence requirements to the other elements present.

19. The process of claim 18 wherein the solution is formed by:
a) preparing a separate solution of the vanadium compound, a separate solution of the antimony compound and a separate solution of the compound of M; and
b) mixing the separate solutions together.

20. The process of claim 18 wherein the vanadium compound, the antimony compound and the compound of M is dissolved in water, alcohol or a mixtures thereof.

21. The process of claim 18 wherein the vanadium compound, the antimony compound and the compound of M is dissolved in acid or alkali.

22. The process of claim 18 wherein the solution is heated to a temperature of from 50 to 90° C.

23. The process of claim 18 wherein the vanadium compound is ammonium metavanadate, vanadyl acetylacetonate, vanadyl chloride or vanadium pentafluoride.

24. The process of claim 18 wherein the antimony compound is an antimony oxide, an antimony halide or an antimony oxyhalide.

25. The process of claim 24 wherein the antimony compound is antimony oxide, antimony trichloride, antimony pentachloride or antimony oxychloride.

26. The process of claim 18 wherein the compound of M is a nitrate, chloride, carbonate, oxalate or hydroxide.

27. The process of claim 18 wherein the base is ammonium hydroxide, ammonium carboxylate, urea or alcohol.

28. The process of claim 27 wherein the ammonium carboxylate is ammonium acetate, ammonium tartrate or ammonium citrate.

29. The process of claim 18 wherein the base is added and mixed to obtain and maintain a pH of from 5 to 10.

30. The process of claim 29 wherein the pH is 8.

31. The process of claim 18 wherein the precipitated hydroxides are separated from liquid by filtration or evaporation.

32. The process of claim 18 wherein the hydroxides are dried at atmospheric pressure and a temperature of from 30 to 200° C.

33. The process of claim 32 wherein the hydroxides are dried at a temperature of from 100 to 150° C.

34. The process of claim 18 wherein the hydroxides are calcined at a temperature from 600 to 950° C.

35. The process of claim 18 wherein the hydroxides are calcined at a temperature from 650 to 850° C.

36. The process of claim 18 wherein the hydroxides are calcined in air.

37. The process of claim 18 wherein the solution is formed of a vanadium compound, an antimony compound and one compound of M and at least one compound of M' and wherein the catalyst is of the formula:

$$VSb_aM_bM'_{b'}O_x$$

wherein M and M' are selected from the group consisting of magnesium, aluminum, zirconium, silicon, hafnium, titanium and niobium and are different and b' is 0 to 50.

38. The process of claim 37 wherein the solution is formed by:
a) preparing a separate solution of the vanadium compound, a separate solution of the antimony compound, a separate solution of the compound of M and a separate solution of the compound of M'; and
b) mixing the separate solutions together.

39. The process of claim 37 wherein the vanadium compound, the antimony compound, the compound of M and the compound of M' is dissolved in water, alcohol or mixtures thereof.

40. The process of claim 37 wherein the vanadium compound, the antimony compound, the compound of M and the compound of M' is dissolved in acid or alkali.

41. The process of claim 37 wherein the solution is heated to a temperature of from 50 to 90° C.

42. The process of claim 37 wherein the vanadium compound is ammonium metavanadate, vanadyl acetylacetonate, vanadyl chloride or vanadium pentafluoride.

43. The process of claim 37 wherein the antimony compound is an antimony oxide, an antimony halide or an antimony oxyhalide.

44. The process of claim 43 wherein the antimony compound is antimony oxide, antimony trichloride, antimony pentachloride or antimony oxychloride.

45. The process of claim 37 wherein the compound of M is a nitrate, chloride, carbonate, oxalate or hydroxide.

46. The process of claim 37 wherein the compound of M' is a nitrate, chloride, carbonate, oxalate or hydroxide.

47. The process of claim 37 wherein the base is ammonium hydroxide, ammonium carboxylate, urea or alcohol.

48. The process of claim 45 wherein the ammonium carboxylate is ammonium acetate, ammonium tartrate or ammonium citrate.

49. The process of claim 37 wherein the base is added and mixed to obtain and maintain a pH of from 5 to 10.

50. The process of claim 49 wherein the pH is 8.

51. The process of claim 37 wherein the precipitated hydroxides are separated from liquid by filtration or evaporation.

52. The process of claim 37 wherein the hydroxides are dried at atmospheric pressure and a temperature of from 30 to 200° C.

53. The process of claim 52 wherein the hydroxides are dried at a temperature of from 100 to 150° C.

54. The process of claim 37 wherein the hydroxides are calcined at a temperature of from 600 to 950° C.

55. The process of claim 37 wherein the hydroxides are calcined at a temperature of from 650 to 850° C.

56. The process of claim 37 wherein the hydroxides are calcined in air.

57. The process of claim 18 wherein the catalyst additionally comprises a compound of Q which is added and precipitated with the other elements or is impregnated on the solid before or after the calcination step wherein Q is selected from the group consisting of rhenium, tungsten, molybdenum, tantalum, manganese, phosphorus, cerium, tin, boron, scandium, bismuth, gallium, indium, iron, chromium, lanthanum, yttrium, zinc, cobalt, nickel, cadmium, copper, strontium, barium, calcium, silver, potassium, sodium and cesium to form a catalyst of the formula:

$$VSb_aM_bQ_cO_x$$

and wherein c is 0 to 10.

58. The process of claim 57 wherein the solution is formed by:
a) preparing a separate solution of the vanadium compound, a separate solution of the antimony compound, a separate solution of the compound of M' and a separate solution of the compound of Q; and
b) mixing the separate solutions together.

59. The process of claim 57 wherein the vanadium compound, the antimony compound, the compound of M and the compound of Q is dissolved in water, alcohol or a mixtures thereof.

60. The process of claim 57 wherein the vanadium compound, the antimony compound, the compound of M and the compound of Q is dissolved in acid or alkali.

61. The process of claim 57 wherein the solution is heated to a temperature of from 50 to 90° C.

62. The process of claim 57 wherein the vanadium compound is ammonium metavanadate, vanadyl acetylacetonate, vanadyl chloride or vanadium pentafluoride.

63. The process of claim 57 wherein the antimony compound is an antimony oxide, an antimony halide or an antimony oxyhalide.

64. The process of claim 63 wherein the antimony compound is antimony oxide, antimony trichloride, antimony pentachloride or antimony oxychloride.

65. The process of claim 57 wherein the compound of M is a nitrate, chloride, carbonate, oxalate or hydroxide.

66. The process of claim 57 wherein the compound of Q is a nitrate, chloride, carbonate, oxalate or hydroxide.

67. The process of claim 57 wherein the base is ammonium hydroxide, ammonium carboxylate, urea or alcohol.

68. The process of claim 67 wherein the ammonium carboxylate is ammonium acetate, ammonium tartrate or ammonium citrate.

69. The process of claim 57 wherein the base is added and mixed to obtain and maintain a pH of from 5 to 10.

70. The process of claim 69 wherein the base is added and mixed to obtain and maintain a pH of 8.

71. The process of claim 57 wherein the precipitated hydroxides are separated from liquid by filtration or evaporation.

72. The process of claim 57 wherein the hydroxides are dried at atmospheric pressure and a temperature of from 30 to 200° C.

73. The process of claim 72 wherein the hydroxides are dried at a temperature of from 100 to 150° C.

74. The process of claim 57 wherein the hydroxides are calcined at a temperature of from 600 to 950° C.

75. The process of claim 57 wherein the hydroxides are calcined at a temperature of from 650 to 850° C.

76. The process of claim 57 wherein the hydroxides are calcined in air.

77. The process of claim 57 wherein a compound of Q is impregnated before or after the calcination step.

78. The process of claim 77 wherein Q is impregnated after the calcination step to form a solid and the process additionally comprises calcining the solid at a temperature from 600 to 950° C.

79. The process of claim 78 wherein the additional calcination step is at a temperature of below 850° C.

80. The process of claim 18 wherein the catalyst additionally comprises compounds of Q and Q' which are added and precipitated with the other elements or are impregnated on the solid before or after the calcination step wherein Q and Q' are each selected from the group consisting of rhenium, tungsten, molybdenum, tantalum, manganese, phosphorus, cerium, tin, boron, scandium, bismuth, gallium, indium, iron, chromium, lanthanum, yttrium, zinc, cobalt, nickel, cadmium, copper, strontium, barium, calcium, silver, potassium, sodium and cesium, to form a catalyst of the formula $$VSb_aM_bQ_cQ'_{c'}O_x$$

and wherein c and c' are 0 to 10.

81. The process of claim 80 wherein the solution is formed by:
a) preparing a separate solution of the vanadium compound, a separate solution of the antimony compound, a separate solution of the compound of x, a separate solution of the compound of Q and a separate solution of the compound of Q'; and
b) mixing the separate solutions together.

82. The process of claim 80 wherein the vanadium compound, the antimony compound, the compound of M, the compound of Q and the compound of Q' is dissolved in water, alcohol or a mixtures thereof.

83. The process of claim 80 wherein the vanadium compound, the antimony compound, the compound of M and the compound of Q and the compound of Q' is dissolved in acid or alkali.

84. The process of claim 80 wherein the solution is heated to a temperature of from 50 to 90° C.

85. The process of claim 80 wherein the vanadium compound is ammonium metavanadate, vanadyl acetylacetonate, vanadyl chloride or vanadium pentafluoride.

86. The process of claim 80 wherein the antimony compound is an antimony oxide, an antimony halide or an antimony oxyhalide.

87. The process of claim 80 wherein the antimony compound is antimony oxide, antimony trichloride, antimony pentachloride or antimony oxychloride.

88. The process of claim 80 wherein the compound of M is a nitrate, chloride, carbonate, oxalate or hydroxide.

89. The process of claim 80 wherein the compound of Q is a nitrate, chloride, carbonate, oxalate or hydroxide.

90. The process of claim 80 wherein the compound of Q' is a nitrate, chloride, carbonate, oxalate or hydroxide.

91. The process of claim 80 wherein the base is ammonium hydroxide, ammonium carboxylate, urea or alcohol.

92. The process of claim 91 wherein the ammonium carboxylate is ammonium acetate, ammonium tartrate or ammonium citrate.

93. The process of claim 80 wherein the base is added and mixed to obtain and maintain a pH of from 5 to 10.

94. The process of claim 93 wherein the base is added and mixed to obtain and maintain a pH of 8.

95. The process of claim 80 wherein the precipitated hydroxides are separated from liquid by filtration or evaporation.

96. The process of claim 80 wherein the hydroxides are dried at atmospheric pressure and a temperature of from 30 to 200° C.

97. The process of claim 96 wherein the hydroxides are dried at a temperature of from 100 to 150° C.

98. The process of claim 80 wherein the hydroxides are calcined at a temperature of from 600 to 950° C.

99. The process of claim 80 wherein the hydroxides are calcined at a temperature of from 650 to 850° C.

100. The process of claim 80 wherein the hydroxides are calcined in air.

101. The process of claim 80 wherein a compound of Q is impregnated before or after the calcination step.

102. The process of claim 101 wherein Q is impregnated after the calcination step to form a solid and the process additionally comprises calcining the solid at a temperature from 600 to 950° C.

103. The process of claim 102 wherein the additional calcination step is at a temperature of below 850° C.

104. The process of claim 80 wherein compounds of Q and Q' are impregnated before or after the calcination step.

105. The process of claim 104 wherein the compounds of Q and Q' are impregnated after the calcination step to form a solid and the process additionally comprises calcining the solid at a temperature from 600 to 950° C.

106. The process of claim 105 wherein the additional calcination step is at a temperature of below 850° C.

107. A process for ammoxidation of alkanes and olefins comprising:
contacting a mixture of an alkane or olefin, ammonia and molecular oxygen in the gas phase with a catalyst composition of the formula:

$$VSb_aM_bO_x$$

wherein V is vanadium, Sb is antimony, M is at least one element selected from the group consisting of magnesium, aluminum, zirconium, silicon, hafnium, titanium and niobium, a is from 0.5 to 20, b is 2 to 50, and x is determined by the valence requirements of the other elements present.

108. The process of claim 107 wherein the catalyst is in a fixed bed, fluidized bed or a moving bed.

109. The process of claim 107 wherein the mole ratio of alkane to ammonia is in the range from 0.5 to 10.

110. The process of claim 109 wherein the mole ratio of alkane to ammonia is in the range from 1 to 2.5.

111. The process of claim 107 wherein the mole ratio of alkane to oxygen is in the range from 0.1 to 10.

112. The process of claim 111 wherein the mole ratio of alkane to oxygen is in the range from 0.5 to 2.

113. The process of claim 107 additionally comprising a diluent in the gas phase selected from the group consisting of nitrogen, helium, argon, carbon dioxide and water.

114. The process of claim 113 wherein the mole ratio of alkane to diluent is in the range from 0 to 20.

115. The process of claim 114 wherein the mole ratio of alkane to diluent is in the range from 0 to 10.

116. The process of claim 107 wherein the alkane has from two to eight carbon atoms.

117. The process of claim 116 wherein the alkane is propane or isobutane.

118. The process of claim 107 wherein the contact occurs at a temperature range from 350 to 550° C.

119. The process of claim 118 wherein the temperature range is from 425 to 500° C.

120. The process of claim 107 wherein the contact occurs at a pressure from 1 to 40 psig.

121. The process of claim 120 wherein the pressure is from 1 to 20 psig.

122. The process of claim 121 wherein the pressure is atmospheric.

123. The process of claim 107 wherein the contact time is from 0.01 to 10 seconds.

124. The process of claim 123 wherein the contact time is from 0.05 to 8 seconds.

125. The process of claim 124 wherein the contact time is from 0.1 to 5 seconds.

126. The process of claim 107 wherein the catalyst composition is of the formula:

$$VSb_aM_bM'_{b'}O_x$$

wherein M and M' are each one element selected from the group consisting of magnesium, aluminum, zirconium, silicon, hafnium, titanium and niobium and b' is 0 to 50.

127. The process of claim 107 wherein the catalyst composition is of the formula:

$$VSb_aM_bQ_cO_x$$

wherein Q is at least one element selected from the group consisting of rhenium, tungsten, molybdenum, tantalum, manganese, phosphorus, cerium, tin, boron, scandium, bismuth, gallium, indium, iron, chromium, lanthanum, yttrium, zinc, cobalt, nickel, cadmium, copper, strontium, barium, calcium, silver, potassium, sodium and cesium and c is 0 to 10.

128. The process of claim 107 wherein the catalyst composition is of the formula:

$$VSb_aM_bQ_cQ'_{c'}O_x$$

wherein Q and Q' are each one element selected from the group consisting of rhenium, tungsten, molybdenum, tantalum, manganese, phosphorus, cerium, tin, boron, scandium, bismuth, gallium, indium, iron, chromium, lanthanum, yttrium, zinc, cobalt, nickel, cadmium, copper, strontium, barium, calcium, silver, potassium, sodium and cesium, c is 0 to 10 and c' is 0 to 10.

* * * * *